United States Patent [19]
Krieger et al.

[11] Patent Number: 5,624,904
[45] Date of Patent: Apr. 29, 1997

[54] METHOD FOR TREATING GRAM POSITIVE SEPTICEMIA

[75] Inventors: Monty Krieger, Needham, Mass.; Keith A. Joiner, New Haven, Conn.

[73] Assignees: Massachusetts Institute of Technology, Cambridge, Mass.; Yale University, New Haven, Conn.

[21] Appl. No.: 154,365

[22] Filed: Nov. 17, 1993

[51] Int. Cl.$^6$ ................................................ A61K 38/16
[52] U.S. Cl. ................................. 514/21; 514/8; 514/12; 424/851
[58] Field of Search ........................... 514/8, 12, 21; 424/85.1

[56] References Cited

U.S. PATENT DOCUMENTS 5,234,912  8/1993  Marra et al. .............................. 514/21

FOREIGN PATENT DOCUMENTS 8912644  12/1989  WIPO.
9214482  9/1992  WIPO.

OTHER PUBLICATIONS

Acton, S., et al, "The collagenous domains of macrophage scavenger receptors and complement component C1q mediate their similar, but not identical, binding specificities for polyanionic ligands", 268 *J. Biol. Chem.* 3530-3537 (1993). This paper was published less than one year before the filing date of the present application.

Ashkenas, J., et al., "Structures and high and low affinity ligand binding properties of murine type I and type II macrophage scavenger receptors", *J. Lipid Res.*, 983-1000 (1993). This paper was published less than one year before the filing date of the present application.

Brown, M.S., and J.L. Goldstein, "Lipoprotein metabolism in the macrophage: mplications for cholesterol deposition in atherosclerosis", 52 *Ann. Rev. Biochem.* 223-261 (1983).

Caparon, M.G., et al., "Role of M protein in adherence of group A streptococci", 59 *Infect. Immun.* 1811-1817 (1991).

Clackson, T., et al., "Making Antibody Fragments Using Phase Display Libraries", 352 *Nature* 624-628 (1991).

Dale, D.C., and R.G. Petersdorf, "Septic Shock", *Harrison's Principles of Internal Medicine* 474-478, 11th ed., E. Braunwald et al. eds. (1987).

Daniel, T.O., et al., "Visualization of lipoprotein receptors by ligand blotting", 258(7) *J. Biol. Chem.* 4606-4611 (1983).

Daugherty, B.L., et al., "Polymerase chain reaction facilitates the cloning, CDR-grafting and rapdi expression of a murine monoclonal antibody directed against the CD18 component of leukocyte integrins", 19(9) *Nucl. Acids Res.* 2471-2476 (1991).

Doi, T., et al., "Charged collagen structure mediates the recognition of negatively charged macromolecules by macrophage scavenger receptors", 268(3) *J. Biol. Chem.* 2126-2133 (1993). This paper was published less than one year before the filing date of the present application.

Dresel, H.A., et al., "Binding of acetylated low density lipoprotein and maleylated bovine serum albumin to the rat liver; one or two receptors?", 6 *Embo. J.* 319-326 (1987).

Fischer, W., "Physiology of lipoteichoic acids in bacteria", 29 *Adv. Microb. Physiol.* 233-302 (1988).

Freeman, M., et al., "An ancient, highly conserved family of cysteine–rich protein domains revealed by cloning type I and type II murine macrophage scavenger receptors", 87 *Proc. Natl. Acad. Sci. (USA)* 8810-8814 (1990).

Goldstein, J.L., et al., "Binding site on macrophages that mediates uptake and degradation of acetylated low density lipoprotein producing massive cholesterol deposition", 76(1) *Proc. Natl. Acad. Sci. USA* 333-337 (1979).

Goldstein, J.L., and M.S., Brown, "Familial Hypercholesterolemia", *The Metabolic Basis of Inherited Disease*, 672-713 Stanbury, J.B., et al. eds New York 1983.

Hampton, R.Y., et al., "Lipid a binding sites in membranes of macrophage tumor cells", 263 *J. Biol. Chem.* 14802-14807 (1988).

Hampton, R.Y., et al., "Recognition and plasma clearance of endotoxin by scavenger receptors", 353 *Nature* 342-344 (1991).

Holm, S.E., "Gram-positive microorganisms in sepsis", *Scand. J. Infec. Dis., Suppl.* 68-77 (1982).

Huang, S.C., et al., "Human recombinant monoclonal antibodies to 60kD Ro Autoantigen", Abstract 167, p. 566, American College of Rheumatology, 57th Annual Scientific Meeting, San Antonio (1993).

Kessler, R.E., et al., "Characterization and localization of the enzymatic deacylation of lipoteichoic acid in group A streptococci", 150 *J. Exp. Med.* 1498-1509 (1979).

Kodama, T., et al., "Type I macrophase scavenger receptor contains α–helical and collagen–like coiled coils", 343 *Nature* 531-535 (1990).

Krieger, M., "Molecular flypaper and atherosclerosis: structure of the macrophage scavenger receptor", 17(4) *Trends Biochem. Sci*, 141-146 (1992).

Krieger, M., et al., "Molecular flypaper, host defense, and atherosclerosis, Structure, binding properties, and functions of macrophage scavenger receptors", 268(7) *J. Biol. Chem.* 4569-4572 (1993).

Laemmli, U.K., "Cleavage of structural protein during the assembly of the head of bacteriophage T4", 227 *Nature* 680-685 (1970).

(List continued on next page.)

*Primary Examiner*—Chhaya D. Sayala
*Attorney, Agent, or Firm*—Arnall Golden & Gregory

[57] ABSTRACT

Macrophage scavenger receptor protein or active fragments thereof bind specifically to the lipoteichoic acid residues on the Gram-positive bacterial cell wall. This protein or active fragments thereof can be used in a variety of methods including methods to specifically purify lipoteichoic acid, to preferentially label or detect lipoteichoic acid or lipoteichoic acid-containing compounds or cells, and to treat patients having Gram-positive bacterial infections such as septicemia and associated pathophysiological states such as septic shock.

8 Claims, 1 Drawing Sheet

OTHER PUBLICATIONS

McCafferty, J., et al., "Phage antibodies; filamentous phage displaying antibody variable domains", 348 *Nature* 552–554 (1990).

Mahlev, R.W., et al., "Alterations in metabolic activity of plasma lipoproteins following selective chemical modification of the apoproteins", 348 *Ann. N.Y. Acad. Sci.* 265–280 (1980).

Nagelkerke, J.F., and T.J. van Berkel, "Rapid transport of fatty acids from rat liver endothelial to parenchymal cells after uptake of cholesteryl ester–labeled acetylated LDL", 875 *Biochim. Biophys. Acta* 593–598 (1986).

Norman, D.J., et al., "Consensus statement regarding OKT3–induced cytokine release syndrome and human anti-mouse antibodies", 25(2)(Supp. 1) *Transplant Proc.* 89–92 (1993).

Ofek, I., et al., "Cell membrane–binding properties of group A streptococcal lipoteichoic acid", 141 *J. Exp. Med.* 990–1003 (1975).

Pitas, R.E., et al., "Uptake of chemically modified low density lipoproteins in vivo is mediated by specific endothelial cells", 100 *J. Cell Biol.* 103–117 (1985).

Raetz, C.R.H., et al., "Gram–negative endotoxin; A biologically active lipid", 53 Cold Spring Harbor Symp. Quant. Biol. 973–982 (1988).

Resnick, D., et al., "Secreted extracellular domains of macrophase scavenger receptors form elongated trimers which specifically bind crocidolite asbestos", 268 (5) *J. Biol. Chem.* 3538–3545 (1993).

Rohrer, L., et al., "Coiled–coil fibrous domains mediate ligand binding by macrophage scavenger receptor type II", 343 *Nature* 570–572 (1990).

Sastry, K., and R.A. Ezekowitz, "Collectins: pattern recognition molecules involved in first line host defense", 5(1) *Curr. Opin. Immunol.* 59–66 (1993).

Schneider, W.J., et al., "Partial purification and characterization of the low density lipoprotein receptor from bovine adrenal cortex", 255 *J. Biol. Chem.* 11442–11447 (1980).

Simpson, W.A., et al., "Binding of streptococcal lipoteichoic acid to the fatty acid binding sites on serum albumin", 255 *J. Biol. Chem.* 6092–6097 (1980).

Steinberg, D., et al., "Beyond cholesterol. Modifications of low–density lipoprotein that increase its atherogenicity", 320(14) *N. Engl. J. Med.* 915–924 (1989).

Sutcliffe, I.C., and N. Shaw, "Atypical lipoteichoic acids of gram–positive bacteria", 173 *J. Bacteriol.* 7065–7069 (1991).

Van Berkel, T.J.C., et al., "Different fate in vivo of oxidatively modified low density lipoprotein and acetylated low density lipoprotein in rats. Recognition by various scavenger receptors on Kupffer and endothelial liver cells", 266(4) *J. Biol. Chem.* 2282–2289 (1991).

Werner, R.G., et al., "Safety and economic aspects of continuous mammalian cell culture", 22 *J. Biotechnology* 51–68 (1992).

Wessels, M.R., et al., "Hyaluronic acid capsule is a virulence factor for mucoid group A streptococci", 88 *Proc. Natl. Acad. Sci.* 8317–8321 (1991).

Wicken, A.J., and K.W. Knox, "Lipoteichoic acids: A new class of bacterial antigen", 187 *Science* 1161–1167 (1975).

Bone, Roger C, Annals of Internal Medicine, vol. 115(6), pp. 457–469, 1991.

Kilbourn, Robert C. et al., Jour. of The National Cancer Institute, vol. 84(11), pp. 827–831, 1992.

Natanson, Charles et al., Annals of Internal Medicine, vol. 120(9), pp. 771–783, 1994.

The Economist, "Panic in the Petri Dish", pp. 61–62, Jul. 23, 1994.

Cross, Alan S et al., Infection and Immunity, vol. 61, No. 7, pp. 2741–2747, Jul. 1993.

Petros, ANdy et al., The Lancet, vol. 338, pp. 1557–1448, 1991.

Hampton et al., J. Biol. Chem., vol. 266(29), pp. 19499–19509, 1991.

Van Lenten et al., I. Immunology, vol. 134(6), pp. 3718–3721, 1985.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2037 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: homo sapien ( v i i ) IMMEDIATE SOURCE:
        ( A ) LIBRARY: THP-1

( x ) PUBLICATION INFORMATION:
        ( A ) AUTHORS: Ashkenas, et al.
        ( C ) JOURNAL: J. Lipid Res.
        ( D ) VOLUME: 34
        ( F ) PAGES: 983-1000
        ( G ) DATE: 1993
        ( K ) RELEVANT RESIDUES IN SEQ ID NO:1: FROM 1 TO 2037

( x i ) SEQUENCE DESCRIPTION: SEQ ID NO:1:

```
AGAGAAGTGG  ATAAATCAGT  GCTGCTTTCT  TTAGGACGAA  AGAAGTATGG  AGCAGTGGGA          60
```

| | | | | | | |
|---|---|---|---|---|---|---|
| TCACTTTCAC | AATCAACAGG | AGGACACTGA | TAGCTGCTCC | GAATCTGTGA | AATTTGATGC | 120 |
| TCGCTCAATG | ACAGCTTTGC | TTCCTCCGAA | TCCTAAAAAC | AGCCCTTCCC | TTCAAGAGAA | 180 |
| ACTGAAGTCC | TTCAAAGCTG | CACTGATTGC | CCTTTACCTC | CTCGTGTTTG | CAGTTCTCAT | 240 |
| CCCTCTCATT | GGAATAGTGG | CAGCTCAACT | CCTGAAGTGG | GAAACGAAGA | ATTGCTCAGT | 300 |
| TAGTTCAACT | AATGCAAATG | ATATAACTCA | AAGTCTCACG | GGAAAAGGAA | ATGACAGCGA | 360 |
| AGAGGAAATG | AGATTTCAAG | AAGTCTTTAT | GCAACACATG | AGCAACATGG | AGAAGAGAAT | 420 |
| CCAGCATATT | TTAGACATGG | AAGCCAACCT | CATGGACACA | GAGCATTTCC | AAAATTTCAG | 480 |
| CATGACAACT | GATCAAAGAT | TTAATGACAT | TCTTCTGCAG | CTAAGTACCT | TGTTTCCTC  | 540 |
| AGTCCAGGGA | CATGGGAATG | CAATAGATGA | AATCTCCAAG | TCCTTAATAA | GTTTGAATAC | 600 |
| CACATTGCTT | GATTTGCAGC | TCAACATAGA | AAATCTGAAT | GGCAAAATCC | AAGAGAATAC | 660 |
| CTTCAAACAA | CAAGAGGAAA | TCAGTAAATT | AGAGGAGCGT | GTTACAATG  | TATCAGCAGA | 720 |
| AATTATGGCT | ATGAAAGAAG | AACAAGTGCA | TTTGGAACAG | GAAATAAAAG | GAGAAGTGAA | 780 |
| AGTACTGAAT | AACATCACTA | ATGATCTGAG | ACTGAAAGAT | TGGGAACATT | CTCAGACCTT | 840 |
| GAGAAATATC | ACTTTAATTC | AAGGTCCTCC | TGGACCCCG  | GGTGAAAAAG | GAGATCGAGG | 900 |
| TCCCACTGGA | GAAAGTGGTC | CACGAGGATT | TCCAGGTCCA | ATAGGTCCTC | CGGGTCTTAA | 960 |
| AGGTGATCGG | GGAGCAATTG | GCTTTCCTGG | AAGTCGAGGA | CTCCCAGGAT | ATGCCGGAAG | 1020 |
| GCCAGGAAAT | TCTGGACCAA | AAGGCCAGAA | AGGGGAAAAG | GGGAGTGGAA | ACACATTAAC | 1080 |
| TCCATTTACG | AAAGTTCGAC | TGGTCGGTGG | GAGCGGCCCT | CACGAGGGGA | GAGTGGAGAT | 1140 |
| ACTCCACAGC | GGCCAGTGGG | GTACAATTTG | TGACGATCGC | TGGGAAGTGC | GCGTTGGACA | 1200 |
| GGTCGTCTGT | AGGAGCTTGG | GATACCCAGG | TGTTCAAGCC | GTGCACAAGG | CAGCTCACTT | 1260 |
| TGGACAAGGT | ACTGGTCCAA | TATGGCTGAA | TGAAGTGTTT | TGTTTTGGGA | GAGAATCATC | 1320 |
| TATTGAAGAA | TGTAAAATTC | GGCAATGGGG | GACAAGAGCC | TGTTCACATT | CTGAAGATGC | 1380 |
| TGGAGTCACT | TGCACTTTAT | AATGCATCAT | ATTTCATTC  | ACAACTATGA | AATCGCTGCT | 1440 |
| CAAAAATGAT | TTTATTACCT | TGTTCCTGTA | AAATCCATTT | AATCAATATT | TAAGAGATTA | 1500 |
| AGAATATTGC | CCAAATAATA | TTTAGATTA  | CAGGATTAAT | ATATTGAACA | CCTTCATGCT | 1560 |
| TACTATTTTA | TGTCTATATT | TAAATCATTT | TAACTTCTAT | AGGTTTTAA  | ATGGAATTTT | 1620 |
| CTAATATAAT | GACTTATATG | CTGAATTGAA | CATTTGAAG  | TTTATAGCTT | CCAGATTACA | 1680 |
| AAGGCCAAGG | GTAATAGAAA | TGCATACCAG | TAATTGGCTC | CAATTCATAA | TATGTTCACC | 1740 |
| AGGAGATTAC | AATTTTTTGC | TCTTCTTGTC | TTTGTAATCT | ATTTAGTTGA | TTTTAATTAC | 1800 |
| TTTCTGAATA | ACGGAAGGGA | TCAGAAGATA | TCTTTTGTGC | CTAGATTGCA | AAATCTCCAA | 1860 |
| TCCACACATA | TTGTTTTAAA | ATAAGAATGT | TATCCAACTA | TTAAGATATC | TCAATGTGCA | 1920 |
| ATAACTTGTG | TATTAGATAT | CAATGTTAAT | GATATGTCTT | GGCCACTATG | GACCAGGGAG | 1980 |
| CTTATTTTTC | TTGTCATGTA | CTGACAACTG | TTTAATTGAA | TCATGAAGTA | AATTGCC    | 2037 |

( 2 ) INFORMATION FOR SEQ ID NO:2:

( i ) SEQUENCE CHARACTERISTICS:
        ( A ) LENGTH: 451 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v ) FRAGMENT TYPE: N-terminal ( v i ) ORIGINAL SOURCE:
    ( A ) ORGANISM: homo sapien ( x ) PUBLICATION INFORMATION:
    ( A ) AUTHORS: Ashkenas, et al.
    ( C ) JOURNAL: J. Lipid Res.
    ( D ) VOLUME: 34
    ( F ) PAGES: 983-1000
    ( G ) DATE: 1993
    ( K ) RELEVANT RESIDUES IN SEQ ID NO:1: FROM 1 TO 451

( x i ) SEQUENCE DESCRIPTION: SEQ ID NO:2:

```
Met Glu Gln Trp Asp His Phe His Asn Gln Gln Glu Asp Thr Asp Ser
 1               5                  10                 15

Cys Ser Glu Ser Val Lys Phe Asp Ala Arg Ser Met Thr Ala Leu Leu
                20                  25                 30

Pro Pro Asn Pro Lys Asn Ser Pro Ser Leu Asp Glu Lys Leu Lys Ser
                35                  40                 45

Phe Lys Ala Ala Leu Ile Ala Leu Tyr Leu Leu Val Phe Ala Val Leu
    50                  55                 60

Ile Pro Leu Ile Gly Ile Val Ala Ala Gln Leu Leu Lys Trp Glu Thr
65                  70                  75                     80

Lys Asn Cys Ser Val Ser Ser Thr Asn Ala Asn Asp Ile Thr Gln Ser
                85                  90                 95

Leu Tyr Gly Lys Gly Asn Asp Ser Glu Glu Met Arg Phe Gln Glu
                100                 105                110

Val Phe Met Glu His Met Ser Asn Met Glu Lys Arg Ile Gln His Ile
        115                 120                125

Leu Asp Met Glu Ala Asn Leu Met Asp Thr Glu His Phe Gln Asn Phe
    130                 135                 140

Ser Met Thr Thr Asp Gln Arg Phe Asn Asp Ile Leu Leu Gln Leu Ser
145                 150                 155                160

Thr Leu Phe Ser Ser Val Gln Glu His Glu Asn Ala Ile Asp Glu Ile
                165                 170                175

Ser Lys Ser Leu Ile Ser Leu Asn Thr Thr Leu Leu Asp Leu Gln Leu
                180                 185                190

Asn Ile Glu Asn Leu Asn Gly Lys Ile Gln Glu Asn Thr Phe Lys Gln
        195                 200                 205

Gln Glu Glu Ile Ser Lys Leu Glu Glu Arg Val Tyr Asn Val Ser Ala
    210                 215                 220

Glu Ile Met Ala Met Lys Glu Gly Gln Val His Leu Glu Gln Glu Ile
225                 230                 235                240

Lys Gly Glu Val Lys Val Leu Asn Asn Ile Thr Asn Asp Leu Arg Leu
                245                 250                255

Lys Asp Trp Glu His Ser Gln Thr Leu Arg Asn Ile Thr Leu Ile Gln
            260                 265                 270

Gly Pro Pro Gly Pro Pro Gly Glu Lys Gly Asp Arg Gly Pro Thr Gly
        275                 280                 285

Glu Ser Gly Pro Arg Gly Phe Pro Gly Pro Ile Gly Pro Pro Gly Leu
    290                 295                 300

Lys Gly Asp Arg Gly Ala Ile Gly Phe Pro Gly Ser Arg Gly Leu Pro
305                 310                 315                320

Gly Tyr Ala Gly Arg Pro Gly Asn Ser Gly Pro Lys Gly Gln Lys Gly
                325                 330                335

Glu Lys Gly Ser Gly Asn Thr Leu Thr Pro Phe Thr Lys Val Arg Leu
```

|     |     | 340 |     |     |     |     | 345 |     |     |     |     | 350 |     |     |     |
| --- | --- | --- | --- | --- | --- | --- | --- | --- | --- | --- | --- | --- | --- | --- | --- |
| Val | Gly | Gly | Ser | Gly | Pro | His | Glu | Gly | Arg | Val | Glu | Ile | Leu | His | Ser |
|     |     | 355 |     |     |     |     | 360 |     |     |     |     | 365 |     |     |     |
| Gly | Gln | Trp | Gly | Thr | Ile | Cys | Asp | Asp | Asn | Trp | Glu | Val | Arg | Val | Gly |
|     | 370 |     |     |     |     | 375 |     |     |     |     | 380 |     |     |     |     |
| Gln | Val | Val | Cys | Arg | Ser | Leu | Gly | Tyr | Pro | Gly | Val | Gln | Ala | Val | His |
| 385 |     |     |     |     | 390 |     |     |     |     | 395 |     |     |     |     | 400 |
| Lys | Ala | Ala | His | Phe | Gly | Gln | Gly | Thr | Gly | Pro | Ile | Trp | Leu | Asn | Glu |
|     |     |     |     | 405 |     |     |     |     | 410 |     |     |     |     | 415 |     |
| Val | Phe | Cys | Phe | Gly | Arg | Glu | Ser | Ser | Ile | Glu | Glu | Cys | Lys | Ile | Arg |
|     |     |     | 420 |     |     |     |     | 425 |     |     |     |     | 430 |     |     |
| Gln | Trp | Gly | Thr | Arg | Ala | Cys | Ser | His | Ser | Glu | Asp | Ala | Gly | Val | Thr |
|     |     | 435 |     |     |     |     | 440 |     |     |     |     | 445 |     |     |     |
| Cys | Thr | Leu |     |     |     |     |     |     |     |     |     |     |     |     |     |
|     |     | 450 |     |     |     |     |     |     |     |     |     |     |     |     |     |

METHOD FOR TREATING GRAM POSITIVE SEPTICEMIA

The government has rights in this invention arising from the National Institutes of Health, Grant Nos. HL41484 and AI30286 and a National Research Service Award that partially funded the research leading to this invention.

BACKGROUND OF THE INVENTION

This invention relates generally to treatment of Gram-positive bacterial infections and associated disease states, and in particular to use of genetically engineered or purified macrophage scavenger receptor protein for treating Gram-positive infections.

Infection from either Gram-negative or Gram-positive bacteria may be associated with a myriad of pathophysiological disease states. For example, infection with either type of microorganisms may result in septicemia and septic shock.

The bacterial components responsible in large part for the pathophysiological phenomena associated with Gram-negative infections, including septic shock, are endotoxin and its toxic component, lipid A. Endotoxins are the lipopolysaccharides uniquely found on the outer surface of Gram-negative bacteria. The outer monolayer of the outer membrane of most Gram-negative bacteria includes a unique hydrophobic component called lipid A, which is the active moiety of endotoxin.

In septic shock resulting from Gram-negative bacteria, endotoxin, or lipid A, activates phospholipases that degrade cell membrane phospholipids to liberate arachidonic acid that can initiate synthesis and release of leukotrienes, prostaglandins, thromboxanes, and other inflammatory mediators. Infusion of Gram-negative bacteria or endotoxin also stimulates release of catecholamines, glucocorticosteroids, histamine, serotonin, and other vasoactive substances. Further, lipid A and its precursor lipid $IV_A$ are potent activators of monocytic macrophages, in which they stimulate the rapid production of a wide array of immune mediators such as interleukin-1, tumor necrosis factor, and platelet activating factor. These inflammatory mediators have major influences on basic motor tone, microvascular permeability, and the aggregation of leukocytes and platelets, through their effects on endothelial and other cells and the generation of biologically active fragments of complement proteins.

Gram-negative bacterial endotoxin and its toxic component, lipid A, play a critical role in the genesis of endotoxin-induced septic shock. They activate phospholipases which degrade cell membrane phospholipids to liberate inflammatory mediators, which then affect microvascular permeability and the aggregation of leukocytes and platelets through the generation of complement factors. These interaction of proteins converts the endothelial cell surface from an anti- to a procoagulant state that permits intravascular coagulation. Endothelial cells lose their ability to selectively regulate permeability to small physiologic molecules, such as water and nutrients, and, under selected conditions, to larger molecules of blood such as plasma proteins. The cells swell and allow fluid to leak into surrounding tissues, causing hypoxia and parenchymal damage.

Endotoxin and lipid A also participate in the activation of macrophages, stimulating the production and release of cytokines, including interleukin-1 and tumor necrosis factor, which also have significant roles in the syndrome of septic shock with Gram-negative organisms.

Endotoxins and other ligands are bound by scavenger receptors on monocytic macrophages and have been shown to be rapidly cleared from the circulation. Scavenger receptors are homotrimeric integral membrane proteins that bind to diverse, high affinity, polyanionic ligands including (1) chemically modified proteins such as acetylated and oxidized low density lipoprotein (LDL) and maleylated bovine serum albumin (M-BSA), but not their unmodified counterparts; (2) certain polysaccharides such as dextran sulfate, but not chondroitin sulfate; (3) four-stranded polynucleotides including poly G and poly I, but not one- or two-stranded polynucleotides; (4) some anionic phospholipids such as phosphatidylserine; and (5) other macromolecules such as polyvinyl sulfate and crocidolite asbestos.

The combined effects of the vasoactive substances and inflammatory mediators in septic shock are body temperature extremes, altered mental status, decreased urine output, a decreased serum albumin concentration, tachypnea with hypoxemia, tachycardia, hypotension, and eventual circulatory collapse. The high morbidity associated with endotoxin-induced shock remains a major clinical problem, especially in debilitated and immunosuppressed patients such as hospitalized patients with underlying diseases that render them susceptible to blood stream invasion, catheterized and surgical patients, neonates, childbearing women, and elderly men with prostatic obstruction. For a review of septic shock, see D. C. Dale and R. G. Petersdorf, "Septic Shock," *Harrison's Principles of Internal Medicine* 474–478, 11th ed., E. Braunwald et al. eds. (1987).

Septic shock may also result from Gram-positive bacterial infections, notably those due to staphylococci, pneumococci, and streptococci. The mechanisms involved in the genesis and progress of Gram-positive septic shock are less clearly defined and understood than in Gram-negative septic shock. Nonetheless hemodynamic parameters are similar, cytokine (TNF, IL-1) induction is analogous and manifestations of organ damage are the same. The main difference in treatment between Gram negative and Gram positive septicemia is that people have focused on endotoxin rather than the Gram positive bacterial components.

Inhibitors and antagonists of the vasoactive substances involved in septic shock, plasma volume expanders, antiinflammatory and other immune system drugs, and various anti-prostaglandins have been used experimentally and clinically to alter the course of septic shock. Such measures have been only partially successful in controlling the morbidity associated with septicemia and septic shock. Because the pathology proceeds rapidly, treatment of patients must be initiated quickly, and suitably rapid differential diagnosis of Gram-positive and Gram-negative septicemia usually has not been possible because fast diagnostic methods have not been available. Therefore, patients who have been treated with compositions that are effective against Gram-negative but not Gram-positive bacteria do not benefit from the treatment. An example of such a composition is Centoxin™, developed by Centocor Pharmaceuticals. Although initial studies demonstrated efficacy against patients with septicemia, larger scale trials were not construed to be effective because of the lack of efficacy in treating patients with Gram-positive septicemia. Further, effective methods and compositions for treating Gram-positive septicemia have not been available generally. Accordingly, what is needed are methods and compositions for use in treating septicemia and associated disease states.

It is therefore an object of the present invention to provide compositions and methods of use to treat septic shock, caused by Gram-positive and/or Gram-negative bacteria.

It is another object of the present invention to provide a method to identify compositions useful in the treatment of septic shock, caused by Gram-positive and/or Gram-negative bacteria.

SUMMARY OF THE INVENTION

Macrophage scavenger receptor protein or active fragments thereof bind specifically to the lipoteichoic acid residues on the Gram-positive bacterial cell wall. This protein or active fragments thereof can therefore be used in a variety of methods including methods to specifically purify lipoteichoic acid, to preferentially label or detect lipoteichoic acid or lipoteichoic acid-containing compounds or cells, and to treat patients having Gram-positive bacterial infections such as septicemia and associated pathophysiological states such as septic shock. The protein can also be used to screen for other compounds which would be effective in treating Gram-positive septic shock.

Macrophage scavenger receptors exhibit unusually broad binding specificity for polyanionic ligands and have been implicated in atherosclerosis and a variety of host defense functions. A radiolabeled, secreted form of the type I bovine macrophage scavenger receptor in an in vitro binding assay binds to intact Gram-positive bacteria, including *Streptococcus pyogenes, Streptococcus agalactiae, Staphylococcus aureus, Enterococcus hirae*, and *Listeria monocytogenes*. Competition binding studies using purified lipoteichoic acid (LTA), an anionic polymer expressed on the surface of Gram-positive bacteria show that LTAs are scavenger receptor ligands and probably mediate their binding to Gram-positive bacteria. LTAs, for which no host cell receptors have previously been identified, are implicated in the pathogenesis of septic shock due to Gram-positive bacteria. Scavenger receptors may participate in host defense by clearing LTA and/or intact bacteria from tissues and the circulation during Gram-positive sepsis. Scavenger receptors have been previously shown to bind to and play an important role in the clearance of endotoxin (lipopolysaccharide), a surface component of Gram-negative bacteria that also causes shock. Thus, scavenger receptors may provide a general mechanism for macrophage recognition and internalization of pathogens and their cell surface components.

DETAILED DESCRIPTION OF THE INVENTION

Figure 1:
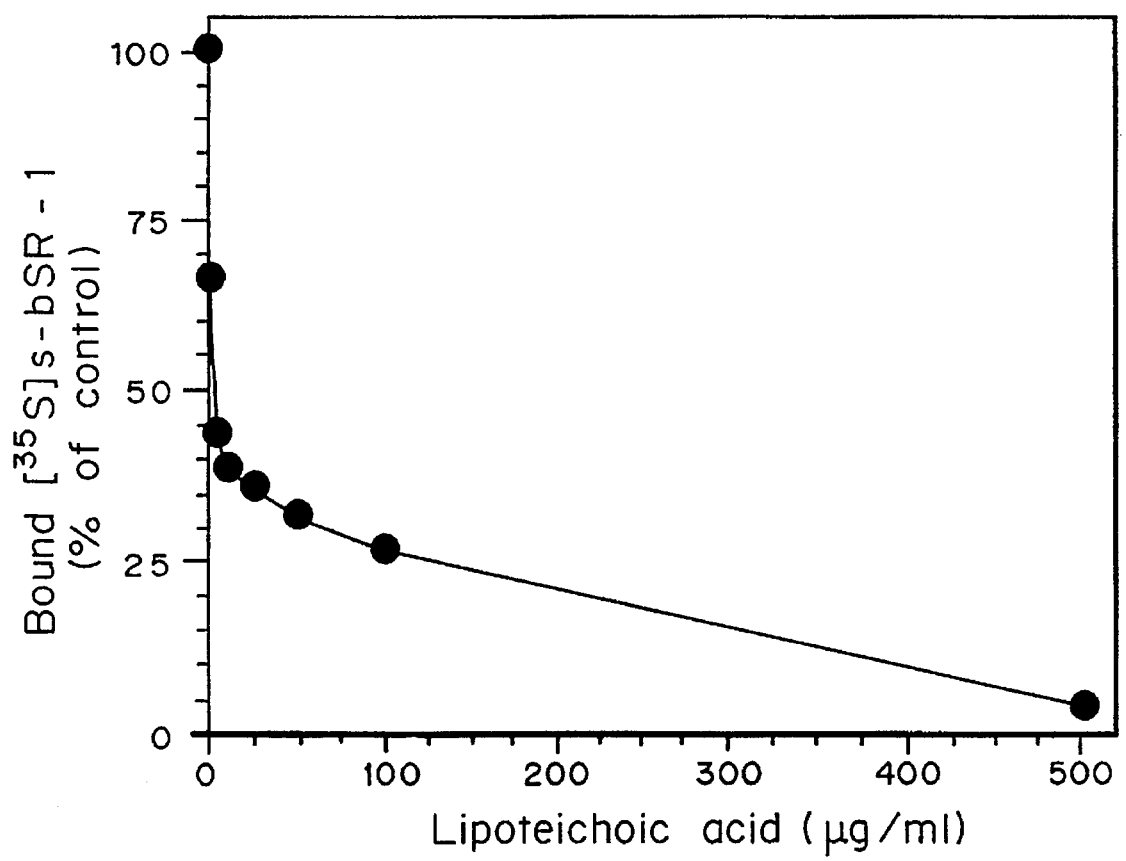
FIG. 1 is a graph illustrating the competitive binding of [$^{35}$S] labeled soluble type I macrophage scavenger receptor ([$^{35}$S]s-bSR-I) (percent of control) by maleylated bovine serum albumin coupled to CNBr-activated Sepharose™ beads (M-BSA beads) in the presence of increasing amounts of lipoteichoic acid (LTA) (mg/ml).

1. Binding of lipoteichoic acid by macrophage scavenger receptor protein (MSRP).

In *Staphylococcus aureus* and many other Gram-positive bacteria, cell wall components include a teichoic acid linked to a peptidoglycan. Lipoteichoic acids (LTA) are amphipathic molecules, typically consisting of a 1–3 phosphodiester-linked polymer of glycerophosphate linked covalently to either a glycolipid or a phosphatidyl glycolipid. The resulting structures possess a backbone of repeating negative charges, a common feature of other MSRP ligands, such as poly G and lipopolysaccharide micelies. LTAs are readily released from bacterial cell surfaces and trigger a variety of pathways in the cellular and humoral immune systems, including cytokine release and nitric oxide production. LTA is also capable of activating the complement cascade by the alternative pathway. Thus, lipoteichoic acid, through complement activation, appears to play a key role in the pathogenssis of Gram-positive septic shock, as endotoxin or lipid A does in Gram-negative septic shock.

It has been discovered that MSRP or active fragments thereof, referred to jointly herein as "MSRP" unless otherwise specified, not only bind the endotoxin or lipid A of Gram-negative bacteria, but also specifically bind intact Gram-positive bacteria that is, the lipoteichoic acid (LTA) moieties on or from the bacterial cell wall. This discovery allows one to use the MSRP or active fragments thereof as therapeutic agents to treat Gram-positive bacterial infections and associated syndromes and disease states such as septicemia and septic shock. Thus, antibodies or other compounds binding to or blocking access to the collagen binding region of the MSRP may be useful as therapeutic agents to treat the same pathophysiological states, or alternatively in models to screen for compounds which would be useful. The receptors may also be useful as reagents to prevent the internalization by macrophages of Gram-positive bacteria which replicate intracellularly (e.g., *Listeria monocytogenes*).

The discovery that the binding between LTA and the MSRP can be blocked can be used in at least two ways: (1) the MSRP or active fragments thereof (as noted above, referred to herein jointly as "MSRP" unless otherwise specified) can be used as reagents to bind to LTA; and (2) LTA or antibodies to the scavenger protein can be used as reagents to bind to the scavenger receptor protein.

Further, isolated MSRP or active fragments thereof may be useful in a variety of other in vitro and in vivo methods, including methods to purify lipoteichoic acid and to label or detect preferentially LTA or LTA-containing compounds or cells.

In addition, the protein can be used as a screen for compounds that may bind the receptor in vivo, thereby blocking binding of the LTA by the receptor protein and uptake of the LTA by the macrophages.

2. Compositions and reagents.
Sources of the MSRP.
a. Purification from natural sources.

In the most preferred embodiment, the therapeutic agent includes the part of the collagen binding domain that binds to LTA. The agent is prepared by isolating native MSRP from macrophages or a related cell line expressing the MSRP on its surface, and then subjecting the purified protein to proteolytic cleavage to remove the intracellular and transmembranous portions of the protein from the extracellular domains. A number of proteolytic enzymes are known in the art that recognize and cleave at a particular amino acid or amino acid sequence. Such commercially available enzymes include trypsin, chymotrypsin, pepsin, Endo Lys C, and Endo Arg C. After digestion, the fragments of the protein are isolated by any number of chromatographic methods, including differential centrifugation, and affinity and column chromatography, among many others.

b. Recombinant methods for obtaining MSRP.

In a preferred embodiment, the therapeutic agent can be obtained from cell lines genetically engineered to express the MSRP or active fragments thereof. For example, a nucleic acid sequence (Sequence ID No. 1) encoding the extracellular domain of the MSRP or a particular active fragment thereof may be used to produce a protein in an appropriate microbial, yeast, insect, or mammalian host cell. To accomplish this, the sequence is inserted into an expression system such as a vector that is suitable for transforming or transfecting a prokaryotic (bacterial) or eucaryotic (yeast, insect, or mammalian) host cell, preferably a mammalian system. Some useful mammalian host cells include Chinese Hamster Ovary (CHO) cells, COS M6 cells, and THP-1 cells. The MSRP may need to be glycosylated to have good binding activity; it probably needs proline-lysine hydroxylation, although neither modification is essential for all purposes. Both insect cells and mammalian cell glycosylate, and the latter hydroxylate lysine and proline, although not always in the same manner.

A major portion of the amino acid sequence of the protein has been derived from the nucleic acid sequence of a cDNA encoding the protein. However, because more than one nucleotide triplet (codon) can encode a single amino acid, a number of different nucleotide sequences can encode a single protein. Hence, the peptide fragment disclosed herein may be encoded by nucleic acid sequences that encode the same amino acid sequences. One skilled in the art, knowing the amino acid sequence of the receptor protein, could synthetically or biosynthetically prepare a functionally equivalent receptor protein having substantially the same biological activity, having modifications in non-conserved amino acids or truncated to remove the membrane binding region.

Form of the MSRP.

a. Full length soluble MSRP.

There are two isoforms of the MSRP, type I and type II. The type I isoform has an apparent molecular weight on SDS polyacrylamide gels of about 220,000 daltons (220 kD). It has an N-terminal cytoplasmic domain, a transmembrane domain followed by a spacer region, and an extracellular long, fibrous stalk composed of an α-helical coiled-coil domain connecting an extracellular collagen-like, triple helix domain. The collagen domain is linked to an extracellular, C-terminal, cysteine-rich domain. The type II receptor is essentially identical to the type I receptor, except that the cysteine-rich domain is replaced by a very short C-terminus. The similar, broad ligand binding specificity of both isoforms is mediated by the short, positively charged collagenous (fibrous) domain in the extracellular region of the receptor. This protein is functional when combined with two other MSRP subunits forming a trimer of subunits, each of which has an apparent molecular weight on SDS-polyacrylamide gels of about 77 kD in the case of the type I receptor, and includes several asparagine (Asn)-linked carbohydrate chains.

As described herein, a preferred therapeutic agent includes at least a portion of the extracellular region of the native human MSRP (amino acid nos. 77–451 of Sequence ID No. 1) responsible for binding negatively charged substances. This extracellular portion must include all or part of the collagen binding domain (amino acid nos. 273–341), and in addition may include the spacer region (amino acid nos. 77–151), all or part of the α-helical coiled coil domain (amino acid nos. 152–272), and/or all or part of the Cys-rich domain (amino acid nos. 342–451). There are slight differences in the numbers of amino acids between species.

The therapeutic agent can be a pharmaceutical composition containing the therapeutic agents or antibodies, alone or in combination with appropriate pharmaceutical stabilization compounds, delivery vehicles, and/or carrier vehicles, and can be prepared according to known methods, as described, for example, in *Remington's Pharmaceutical Sciences* by E. W. Martin.

b. Active fragments of MSRP.

The ligand binding specificity of the MSRP is mediated by the extracellular collagenous (fibrous) domain.

Therefore, at least all or part of the collagen binding domain (amino acid nos. 273–341) must be included in an active fragment of MSRP. An active fragment may also include, in addition, the spacer region (amino acid nos. 77–151), all or part of the α-helical coiled coil domain (amino acid nos. 152–272), and/or all or part of the Cys-rich domain (amino acid nos. 342–451).

As used herein, soluble MSRP includes amino acids 77 to 451 of the human sequence for type I scavenger receptor protein shown in Sequence ID No. 2, as encoded by the nucleotide sequence in Sequence ID No. 1, as well as the type II scavenger receptor (the bovine form having 349 amino acids), equivalent molecules from other species and the forms prepared by substitution of amino acids from one species to the analogous location in the form from a different species, unless otherwise specified.

The ability of the soluble MSRP to block scavenger receptor-mediated cellular metabolism of known MSRP ligands, such as radiolabeled endotoxin, whole Gram-positive bacteria, or LTA, is measured by competitive inhibition assays. The soluble receptor protein is inhibited by the same ligands as the membrane-bound form, as demonstrated by the ability of such ligands to interfere with the binding of labeled soluble forms of the receptor to poly G beads, M-BSA beads, or LTA. For example, the inhibitors poly G, poly I, maleylated BSA, and AC-LDL were successful competitors at 400 μg/ml, while poly C, LDL, and BSA failed to compete. This demonstrates that the soluble receptor protein has similar binding specificity and hence utility as the full-length, membrane-bound form. This bead-binding assay can be used to measure the association of endotoxin, lipid $IV_A$, LTA, and similar molecules, to soluble forms of the MSRP.

The ability of the MSRP to bind lipid $IV_A$ is determined by the methods of Raetz et al., 53 *Cold Spring Harbor Symp. Quant. Biol.* 973–982 (1988) and Hampton et al., 263 *J. Biol. Chem.* 14802–14807 (1988).

The binding activity of the soluble receptor protein can be measured by filter binding and ligand blotting assays performed with minor modification, according to the methods of Schneider et al. (1980) and Daniel et al., 258 *J. Biol. Chem.* 4606–4611 (1983). Ligand binding specificity can also be determined by polynucleic acid affinity chromatography. M-BSA-purified soluble proteins having LTA binding activity in 4 ml of buffer containing 40 mM octyl glucoside, are applied to polynucleic acid coupled agarose columns (AG-POLY series, prepacked column, Pharmacia). After being washed with the same buffer, the bound protein is removed with 5 ml of elution buffer.

c. Immobilized MSRP.

The isolated MSRP and active fragments thereof can be immobilized for use in treatment of septic shock, diagnostic assays, and purification. For example, MSRP or active fragments thereof can be used for affinity column chromatography for LTA or LTA-containing compounds or cells; immunoblots wherein the scavenger molecule is used in place of an antibody to detect the presence of its ligand; Elisa-type assays for LTA and LTA-containing compounds and cells; and removal of LTA and Gram positive bacteria from blood by passage through an extracorporeal reactor containing immobilized MSRP.

Extracorporeal Reactors

Although in one embodiment soluble MSRP or an active fragment thereof is administered to a patient in need of treatment thereby, preferably by intravenous administration in a pharmaceutically acceptable carrier, in some cases it may be preferable to treat the patient by passage of the patient's blood through an extracorporeal reactor having bound thereto MSRP or an active fragment thereof. An example of such a reactor is a kidney dialysis unit in which the protein is immobilized on the polymer membranes (typically cellulose) using standard techniques such as reaction with carboiimidazole or other crosslinking reactions. Immobilization to chromatographic or assay substrates The protein can be similarly immobilized for use as a screen for compounds that may bind the receptor in vivo, thereby blocking binding of the LTA by the receptor protein and uptake of the LTA by the macrophages. For example, MSRP or LTA is immobilized on a substrate such as a 96 well plate or a polystyrene test tube using conventional binding technology. The compound to be tested and the agent which binds the immobilized reagent, either MSRP or LTA, respectively, is then added to the well or test tube under conditions wherein binding occurs, unbound material is removed, and the relative percent binding in the controls versus in the presence of the compound to be tested is compared.

Samples to be tested for the presence of LTA, or Gram positive bacteria, can be tested in an analogous manner, but without the addition of a compound inhibiting binding. In this case, the sample is added to the well or test tube containing the immobilized MSRP under conditions where binding occurs (having pH of approximately 6.5 to 7.5, physiological ionic strength, i.e., 0.15M NaCl).

3. Other reagents that bind to MSRP.

a. Antibodies to MSRP.

Either polyclonal or monoclonal antibodies to MSRP, or fragments thereof, can be generated using standard techniques. These are then humanized for use in treating humans to treat septic shock or remove Gram positive bacteria and/or bacterial components.

Appropriate animals, such as mice, are immunized with the isolated human MSRP. In a preferred method, each mouse is injected biweekly with 50 µg of antibody with no adjuvant over a period of six months. Antibody production in the mice is then assayed using standard techniques for determining the titer of antibodies, for example, by measuring the ability of mouse sera to inhibit the binding of human MSRP to LTA. The mice with the highest titer are then selected for production of hybridomas. Hybridomas are generated using standard techniques to fuse spleen cells from high-titer mice with mouse myeloma cells.

The hybridomas are screened for those producing antibodies. Hybridoma cells secreting selected protective antibodies are used in the production of recombinant antibodies. For example, Pharmacia's (Pharmacia LKB Biotechnology, Sweden) "Recombinant Phage Antibody System" (RPAS) may be used for this purpose. In the RPAS, antibody variable heavy and light chain genes are separately amplified from the hybridoma mRNA and cloned into an expression vector. The heavy and light chain domains are co-expressed on the same polypeptide chain after joining with a short linker DNA which codes for a flexible peptide. This assembly generates a single-chain Fv fragment (ScFv) which incorporates the complete antigen-binding domain of the antibody.

Using the antigen-driven screening system, the ScFv with binding characteristics equivalent to those of the original monoclonal antibody is selected [See, e.g., McCafferty, J., et al., Nature, 348:552–554, 1990; Clackson, T., et al., Nature, 352:624–688, 1991, incorporated herein by reference]. The recombinant ScFv includes a considerably smaller number of epitopes than the intact monoclonal antibody, and thereby represents a much weaker immunogenic stimulus when injected into humans. An intravenous injection of ScFv into humans is, therefore, expected to be more efficient and immunologically tolerable in comparison with currently used whole monoclonal antibodies [Norman, D. J., et al., Transplant Proc., 25, suppl. 1:89–93, 1993].

If necessary, animal antibodies, such as murine antibodies, can be humanized to further reduce the recipient's immune response to the antibodies. A humanized antibody is one in which only the antigen-recognition sites or complementarity-determining hypervariable regions (CDRs) are of non-human origin, and all framework regions (FR) of variable domains are products of human genes. In one method of humanization of an animal monoclonal antibody, RPAS is combined with the CDR grafting method described by Daugherty et al., Nucl. Acids Res., 19:2471–2476, 1991, incorporated herein by reference. Briefly, the variable region DNA of a selected animal recombinant anti-idiotypic ScFv is sequenced by the method of Clackson, T., et al., Nature, 352:624–688, 1991, incorporated herein by reference. Using this sequence, animal CDRs are distinguished from animal framework regions (FR) based on locations of the CDRs in known sequences of animal variable genes. Kabat, H. A., et al., Sequences of Proteins of Immunological Interest, 4th Ed. (U.S. Dept. Health and Human Services, Bethesda, Md., 1987). Once the animal CDRs and FR are identified, the CDRs are grafted onto human heavy chain variable region framework by the use of synthetic oligonucleotides and polymerase chain reaction (PCR) recombination. Codons for the animal heavy chain CDRs, as well as the available human heavy chain variable region framework, are built in four (each 100 bases long) oligonucleotides. Using PCR, a grafted DNA sequence of 400 bases is formed that encodes for the recombinant animal CDR/human heavy chain FR protection.

The expression of recombinant CDR-grafted immunoglobulin gene is accomplished by its transfection into appropriate human cells such as human 293 cells (transformed primary embryonic kidney cells, commercially available from American Type Culture Collection, Rockville, Md. 20852) which secrete fully grafted antibody. See, e.g., Daugherty, B. L., et al., Nucl. Acids Res., 19:2471–2476, 1991, incorporated herein by reference. Alternatively, humanized ScFv is expressed on the surface of bacteriophage and produced in E. coli as in the RPAS method described above.

In a similar fashion to the method described for preparation of the recombinant antibodies, the human ScFv are made and selected on the basis of their affinity for MSRP [See, e.g., Huang, S. C., Koren, E., et al., Human Recombinant Monoclonal Antibodies to 60 kD Ro. Autoantigen, American College of Rheumatology, 57th Annual Scientific Meeting, San Antonio, Nov. 7–11, 1993]. Briefly, RNA enriched in mRNA encoding antibodies is obtained and amplified using PCR. Genes encoding single chain Fv fragments are made by randomly combining the VH and VL products through a linker using PCR. This combinatorial library is then cloned into a phage system, and displayed on the surface of the phage using the method of Cambridge Antibody Technology. Antibody ScFv-bearing phage are enriched by several rounds of growth and screening with MSRP. Individual ScFv are then selected based on binding to MSRP as determined by ELISA. The recombinant ScFv or humanized anti-idiotypic antibodies may be administered intravenously to a recipient in order to treat septic shock by administering an amount effective to bind the bacteria or the bacterial components.

An enzyme linked immunosorbent assay (ELISA) is used as follows to detect and quantify antibodies. ELISA plates are coated with purified MSRP and blocked. The plates are then incubated with corresponding antibodies, preferably of murine origin, which are biotinylated at the Fc fragment using procedures well-known to those skilled in the art, e.g., using the biotinylation kit available from Pierce, Rockford, Ill. The magnitude of inhibition is determined by observation of the colored reaction occurring after an incubation with streptavidin-peroxidase and peroxidase substrate (Kirkegaard and Perry Labs, Gaithesburg, Md.).

These antibodies can be produced in bioreactors in large quantities and processed for the parenteral use in humans according to established procedures, for example, as described by Werner, et al., *J. Biotechnology*, 22:51–63, 1992, the teachings of which are incorporated herein by reference.

4. Methods of treating septicemia.
   a. Pharmaceutical Compositions.

The MSRP or active fragments thereof, antibodies to the MSRP, or compounds inhibiting binding of Gram positive bacteria to MSRP other than antibodies, referred to jointly herein as therapeutic agents unless otherwise specified, can be used for the treatment of pathologies such as septicemia, Gram-positive bacterial infection, Gram-positive septicemia, or Gram-positive or Gram-negative septic shock.

Pharmaceutical compositions containing therapeutic agents or antibodies, alone or in combination with appropriate pharmaceutical stabilization compounds, delivery vehicles, and/or carrier vehicles, are prepared according to known methods, as described, for example, in Remington's *Pharmaceutical Sciences* by E. W. Martin.

The pharmaceutical forms of the therapeutic agent suitable for injectable use include sterile aqueous solutions or dispersions and sterile powders for the extemporaneous preparation of sterile injectable solutions or dispersions. In all cases the form must be sterile and must be fluid to the extent that easy syringability or infusibility exists. It must be stable under the conditions of manufacture and storage and may be preserved against the contaminating action of microorganisms, such as bacteria and fungi.

In one preferred embodiment, the preferred carriers or delivery vehicles for intravenous infusion are physiological saline or phosphate buffered saline. In another preferred embodiment, suitable stabilization compounds, delivery vehicles, and carrier vehicles include, but are not limited to, other human proteins such as albumin. Phospholipid vesicles or liposomal suspensions may also be used as pharmaceutically acceptable carriers or delivery vehicles. These can be prepared according to methods known to those skilled in the art.

b. Treatment regime.

The treatment dosages and frequency of dosage will vary depending on the severity of the bacterial infection. Generally, dosage level is adjusted in frequency, duration, and units in keeping with the severity and duration of each patient's infection and associated symptoms.

In a preferred embodiment, therapeutic agents, alone or in combination with stabilizers, delivery vehicles, and/or carriers, are administered to patients in need of treatment thereof, most preferably by intravenous adminstration.

In a preferred mode of administration of the therapeutic agent, the composition is given intravenously at a preferred dosage in the range from about one to ten mg/kg body weight at intervals of between 12 and 24 hours, depending on the in vivo half-life; and the duration of treatment in days is in the range from one to two days or until the infection is resolved. For example, antibodies are administered in an appropriate pharmaceutical carrier, such as saline. The preferred routes of administration are by intravenous infusion and intravenous injection, although intramuscular injection is possible. It is estimated that an adult human recipient would be treated with a total of 5–8 grams of antibodies, in an appropriate pharmaceutical carrier.

Conditions to be considered in selecting dosage level and duration primarily include the half-life of the therapeutic agent, as well as the therapeutic efficacy. It is to be understood that for any particular subject, specific dosage regimens should be adjusted over time according to the individual patient need and the professional judgment of the person administering or supervising the administration of the compositions, and that the concentration ranges set forth herein are exemplary only and are not intended to limit the scope or practice of the claimed composition. Other concentration ranges and dosage durations can be determined by routine experimentation.

5. Diagnostic uses of MSRP or active fragments thereof.

The MSRP or active fragments thereof can be used for a variety of diagnostic, as well as therapeutic, purposes. In a simple embodiment, insoluble or soluble receptor proteins are harvested and purified from eucaryotic cells that are preferably mammalian, or from eucaryotic or prokaryotic cells engineered by recombinant means to produce such proteins, and used in both labeled, for example fluorescently-, radio-, avidin/strepavidin/biotin-, enzyme- or dye-labeled, and unlabeled states in competitive binding assays to test for the presence of LTA. For example, the collagen binding domain of the receptor protein can be linked to an inert support material as described above for uses in affinity chromatographic methods to isolate lipoteichoic acid (LTA) or LTA-containing compounds and cells, or lipids and lipid-containing substances such as endotoxin; or to purify inhibitors which may be useful diagnostic, analytic, or therapeutic agents.

For example, for diagnostic purposes, as well as for treatment of patients, antibodies are covalently coupled to an insoluble matrix. Suitable antibodies are selected based on their protective activity, affinity, chemical stability and immunoglobulin class. Preferred antibodies are stable IgG antibodies with high binding affinity. These antibodies are purified using procedures well-known to those skilled in the art. Purified antibody may be immobilized using coupling kits consisting of various forms of activated gels, for example, Affi-Gel™ or Affi-Prep™ (Bio-Rad, Richmond, Calif.), ImmunoPure™ Ag/AB Immobilization kits 1,2 and 3 (Pierce, Rockford, Ill.), and appropriate reagents, although other methods of antibody immobilization are well-known to those skilled in the art.

An exemplary assay for LTA-related substances can be carried out as follows. The sample, having an unknown concentration of LTA-related substance, is first contacted with a known quantity of immobilized receptor protein (or analog or a portion thereof containing the epitope and having the ability to bind an LTA-related substance), during which time the LTA-related substance in the sample becomes bound to the receptor protein. The mixture is then treated with a known quantity of labeled analyte which binds to those sites on the fixed support which were unoccupied. Excess label is then washed off, and the quantity of label remaining on the support is inversely proportional to the amount of analyte originally present in the sample.

An exemplary assay for measuring the binding of lipoteichoic acid (LTA) or LTA-containing compounds or cells by MSRP or active fragments thereof can be carried out as follows. A conditioned medium containing a secreted form of the receptor is obtained by incubating transfected eukaryotic cells expressing the secreted receptor in suitable medium, such as Ham's F-12, containing a label such as [$^{35}$S]methionine, collecting the supernatant, adding protease inhibitors, and clarifying the supernatant, for example, by centrifugation. The binding assay for whole cells is as follows. Gram-positive bacteria are incubated under conditions sufficient to allow binding to occur, for example at 4° C. overnight, with labeled conditioned medium containing the receptor. Bacteria and bound receptor are then pelleted by centrifugation, solubilized with detergents, and resolved by gel electrophoresis. Then bound metabolically labeled receptor proteins are visualized, for example, by autoradiography. Suspensions of Sepharose™ beads coupled with other ligands, such as maleylated bovine serum albumin (M-BSA beads) or poly G, can be used in place of bacterial suspensions as controls. Inhibition of the binding of the MSRP to the M-BSA beads is demonstrated by adding increasing amounts of lipoteichoic acid (LTA) to the assay mixture. Inhibition of the binding of the bacteria to the receptor protein is demonstrated by adding another receptor ligand, such as poly G to the assay mixture.

These assays are particularly useful in screening for compounds which inhibit binding of the Gram positive bacteria to MSRP, and therefore uptake and processing by the macrophages. These compounds may be useful in the treatment of septicemia, or in animal models to screen compounds for the treatment of septicemia.

The method for treating septicemia and compositions for use in the method for treatment, as well as diagnostic assays and purification procedures, will be more fully understood by reference to the following non-limiting examples.

EXAMPLE 1

Method of preparing soluble MSRP from native proteins.

The soluble form of the MSRP or active fragments thereof are obtained by enzymatic cleavage of isolated native protein as follows. Membrane proteins from 500 g of liver are prepared essentially by the method of Schneider et al., 225 *J. Biol. Chem.* 11442–11447 (1980)), incorporated herein by reference. The proteins are resuspended in 500 ml of 10 mM Tris-HCl, pH 8, 2 mM CaCl$_2$, 0.15 M NaCl and 1 mM PMSF (Buffer A), sonicated twice, and then dissolved by the addition of 55 ml of 20% Triton X-100 with stirring for 30 min. Insoluble material is removed by centrifugation (33,000 rpm, 1 hr, Beckman Type 35 rotor). The supernatant (500 ml) is applied at 75 ml/hr to an M-BSA-coupled Sepharose™ 4B column (Pharmacia, 9.8×12 cm, containing about 10 mg of M-BSA/ml of gel) which has been equilibrated with Buffer A containing 1% Triton X-100. The column is washed overnight with the same buffer and then washed with two column volumes of Buffer A containing 40 mM octyglucoside. The receptor protein is eluted with Buffer B (1 M NaCl, 20 mM Tris HCl, pH 8, 1 mM CaCl$_2$, 1 mM PMSF, and 40 mM octyglucoside).

The fractions obtained are tested for their ability to bind acetylated low density lipoprotein (AC-LDL) and LTA as described below; those containing AC-LDL and LTA-related substances binding activity are pooled and concentrated using ultrafiltration (Diaflo membrane PM30, Amicon). The sample buffer is changed to 25 mM potassium phosphate, 40 mM octyglucoside, 1 mM PMSF, pH 6.8, using PD10 desalting columns (Pharmacia). The M-BSA affinity purified fraction (50 ml) is then applied to an Ultrogel-Ha (LKB) column (2.5×13 cm) at a flow rate of 75 ml/hr, and the proteins eluted with a gradient of phosphate buffer (25 mM to 350 mM) containing 40 mM octyglucoside.

The 220 kD MSRP is recovered at phosphate concentrations between 100 and 200 mM and is further purified by non-reducing SDS-PAGE on a 3–10% acrylamide gradient gel as described by Laemmli, 227 *Nature* 680–685 (1970), incorporated herein by reference. A 220 kD protein with AC-LDL binding activity is electroeluted from the gel in 0.1% SDS, 10 mM Tris-HCl, pH 8 using an ISCO 1750 electrophoretic concentrator.

The MSRP can also be purified by a combination of M-BSA affinity chromatography and IgG-D1 immunoaffinity chromatography, using an antibody to the MSRP. All procedures are performed at 4° C. One hundred ml of Buffer C (0.1% SDS, 0.1% sodium deoxycholate, 1% Nonidet P40, 50 mM Tris-HCl, pH 8, 150 mM NaCl, and 1 mM PMSF) are added to M-BSA affinity purified proteins from 500 g of liver or lung (or a smaller amount of THP-1 cells) in 100 ml Buffer B. The sample is applied to Sepharose™ 4B (Pharmacia) coupled with IgG-D1 (4 mg antibody/ml gel), prepared as described below, at a flow rate of 50 ml/hr, and recycled overnight. The column is washed consecutively with 50 mi of Buffer C, 50 ml of Buffer D (0.2% Triton X-100, 10 mM Tris-HCl, pH 8), 50 ml of Buffer D containing 2 M NaCl, and 20 ml of Buffer E (40 mM octylglucoside containing 10 mM Tris-HCl, pH 8). The bound proteins are then eluted with 20 ml of Buffer E containing 2 M guanidine thiocyanate. After elution, the buffer is changed to Buffer A containing 40 mM octyglucoside using PD10 columns (Pharmacia).

Isolated MSRP is then subjected to proteolytic cleavage using serine-, sulfhydryl-, metallo-, or aspartyl proteases to cleave the receptor to remove the membrane spanning domain from the extracellular domain containing the ligand binding site.

EXAMPLE 2

Preparation of the soluble MSRP by recombinant DNA technology.

A soluble form of the MSRP was also obtained by using recombinant DNA technology. Methodology for the production of recombinant soluble MSRP, unless otherwise noted, included standard procedures such as those described in Maniatis et el., *Molecular Cloning, A Laboratory Model* Cold Spring Harbor Laboratory (1982); and Davis et al., *Basic Methods In Molecular Biology*, Elsevier Scientific Publishing Co., Inc., N.Y. (YEAR?). The nucleic acid sequence of the MSRP is shown as Sequence ID No. 1.

Vectors for the expression of soluble, secreted MSRP type I (BSRI) and type II (bSRI) were generated as follows. A DNA fragment containing the myelin associated glycoprotein (MAG) leader sequence and a portion of the fibronectin gene were obtained by digesting the vector pMIT (gift from Dr. Richard Hynes, MIT) with BamH1 and Xba1. This was ligated with a pcDNA1 backbone generated by digestion of pXbSR3 (pcDNA1/Type II) with BamH1/Xba1. The pcDNA1 vector is commercially available (Invitrogen); however, the pcDNA1/Type II (pXbSR3) vector has additional features, as described by Rohrer et al., 343 *Nature* 531–535 (1990). The resulting vector is called pCDNA1/MAG.

The pcDNA1/MAG vector was digested with Xho1, Klenow blunted, and digested with Xba1 to yield a linear fragment with a 5' blunt end and a 3' sticky Xba1 end. This construction was then ligated to a Sma1 and Xba1 digested polymerase chain reaction (PCR) product described below, to form the construct called pcDNA1/common. The term "common" refers to the fact that the PCR product contains sequence common to both the type I and the type II bovine MSRP cDNAs.

A region common to secreted bSRI and bSRII was obtained by utilizing PCR technology as described in *PCR Technology; Principles and Applications for DNA Amplification* (Henry R. Erlich, ed.) Stockton Press, (1989), and in Freeman et al., 87 *Proc. Natl. Acad. Sci. (USA)*. 8810–8814 ( ). The oligonucleotides MKSec5' and MKTK8 were used to generate a 620 base pair fragment by PCR using native pcDNAi-bSRI (pXbSR7) as a template. This fragment was digested with SmaI (site in the primer MkSec5') and XbaI (site in the common MSRP cDNA sequence), and ligated to the pcDNA1-MAG construct as described above to generate pcDNA1 common. The pcDNA1/common encodes at its 5' end the MAG leader sequence, which is attached directly to the cDNA that encodes MSRP amino acids 77–227. The construction results in the conversion of the lysine at position 77 of the receptor to the two amino acids, argenine-glycine. This site was expected to be the N-terminal amino acid after the MAG-receptor primary translation product is cleaved during translocation into the endoplasmic reticulum.

The remainder of the secreted BSRI was added by obtaining an Xba1-Xba1 fragment from the full length pcDNA1/ Type I (pXbSR7), as described by Kodama et al., 343 *Nature* 531–535 (1990), encoding the 3' portion of the gene, and ligating it with the Xba1 digested pcDNA1/common vector, resulting in the creation of the construction called pcDNA1/bSR-I-sec. The vector pcNA1/bSR-II-sec was generated identically using an Xba1-Xba1 fragment from pcDNA1/ Type II (pxbSR3), as described by Rohrer et al., 343 *Nature* 531–532 (1990).

The region encoding the secreted BSRI including the MAG leader was excised from pcDNA1/bSR-I-sec with HindIII and ligated with a HindIII digested pRc/CMV (Invitrogen) backbone. Secreted bSRII was transferred to PRc/CMV using an identical strategy.

CHO host cells were transfected with the pRc/CMV/bSR-I-sec vector using the polybrene method described in Maniatis et al., *Molecular Cloning. A Laboratory Manual* 16–47, Cold Spring Harbor Laboratory (1982). Neomycin-resistant cells were selected using G418 (Gibco BRL, Gaithersberg, Md.), a neomycin analog. G418-resistant colonies were picked at random and screened for expression of the protein product using a 30 minute pulse with 400 μCi/mi $^{35}$S-methionine, followed by lysis and immunoprecipitation with an anti-peptide antibody that was raised against a peptide in the Cys rich domain.

Media from a positive colony were examined for the presence of secreted BSR-I as follows. The cells were grown in the presence of 80 μCi/ml $^{35}$S-methionine for 5 hours, at which time the media was harvested. PMSF was added to 1 mM and leupeptin to 0.1 mM. The medium was then centrifuged at 1500×g for 15 minutes to remove cellular debris. The labeled medium was diluted 3:1 with buffer A (20 mM Tris, pH 8.0, 150 mM NaCl, 1 mM $CaCl_2$) containing 2 mg/ml bovine serum albumin. To this was added 25 μl AG-Poly G beads (Pharmacia) that had been washed in buffer A. This mixture was vortexed and placed on a rotator at 4° C. overnight. The beads were then washed twice with buffer A and protein eluted by the addition of 30 μl sample buffer and boiling. The eluate was run on an 8% Laemmli gel, which was dried and exposed to preflashed Kodak XR7 film. A band of 72 kD was seen in transfected cells but not in untransfected CHO cells.

EXAMPLE 3

Method for measuring the binding of MSRP (s-bSR-I) to microbes (microbial binding assay).

a. Method of growing Gram-positive bacteria.

Gram-positive bacteria were obtained as follows. *Streptococcus pyogenes* strains T1/195/2, S43/192/4, J17E/165/3, T2/44/RB4/119, and T22/76/2, in addition to a spontaneous M-protein negative mutant (T28/51/4), with a large deletion in the mry/emm operon, and its parent wild type (T28/150/A/S), were provided by Vincent Fischetti (Rockefeller University, New York City, N.Y.). A Tn916 mutant (JRS75) of S. pyogenes that lacks both M protein and carboxypeptidase (M. G. Caparon et al., 59 *Infect. Immun.* 1811–1817 (1991)) and its type 6 parent strain (JRS4) were donated by June Scott (Emory University, Atlanta, Ga.). *S. pyogenes* wild-type strain 87–282 and its acapsular Tn916 mutant, TX-4 (M. R. Wessels et al., 88 *Proc. Natl. Acad. Sci.* 8317–8321 (1991)); and *Streptococcus agalactiae* strains A909 (type Ia) and COH 31-15 (unencapsulated Tn 918 mutant of type II strain COH 15) were provided by Mike Wessels (Channing Laboratory, Boston, Mass.). *S. agalactiae* strains 110 and 181 were donated by Steve Mattingly (San Antonio, Tex.). *Staphylococcus aureus* capsular type 5 strain Reynolds and its transconjugate mutants, strains JL 236 (Tn-918-induced capsule deficient mutant) and JL 240 (EMS-derived capsule negative mutant) in addition to type 8 strain Becker and its mutant, JL 252 (Tn-551-induced capsule negative mutant) were donated by Jean Lee (Channing Laboratory, Boston, Mass.). *Streptococcus mutans* (ATCC 25175), *Enterococcus hirae* (ATCC 9790), *Listeria monocytogenes* (ATCC 43251), and *Bacillus subtilis* (ATCC 6633) were obtained from the American Type Tissue Collection (Rockville, Md.). Strains of *Streptococcus pneumoniae* (rough, type 6, type 8) were obtained at the Massachusetts Institute of Technology.

Gram-positive bacteria were grown overnight either on LB agar plates (*L. monocytogenes, B. subtilis*) or on 5% sheep blood agar plates (all other organisms). Fresh colonies were inoculated into Todd Hewitt Broth (DIFCO) and were grown to stationary phase (16–18 hours; $1×10^9$ CFU/1 ml) at 37° C. without shaking. Initial experiments indicated greater binding of MSRP to organisms grown to stationary phase compared to organisms used at log phase. Thus, stationary phase organisms were used in all experiments, although results were similar for log phase organisms.

All bacterial strains were harvested by centrifugation at 3500×g for 10 minutes and washed twice in cold Buffer B (20 mM Tris base at pH 8.0/150 mM NaCl/0.05% $NAN_3$) before resuspending to a final density of approximately $1×10^9$ bacteria/ml (O.D.$_{600}$=2.0).

Organisms were labeled with fluorescein isothiocyanate (FITC) as follows. Stationary phase *S. pyogenes* were suspended in PBS to O.D.$_{600}$=1.0. To 5 ml of organisms, 5 μl of FITC (100 mg/ml in DMSO) was added, and the mixture was incubated at 37° C. for 60 minutes with periodic vortexing. Organisms were washed twice in PBS, then suspended in Ham's F12 containing 10% fetal calf serum.

b. Preparation of metabolically labeled soluble bovine MSRP, type I (s-bSR-I).

Untransfected Chinese hamster ovary (CHO) cells and transfected CHO cells (CHO[s-bSRI]-A2) expressing a truncated, secreted form of the type I bovine MSRP (s-bSR-I) were described previously by Resnick, et al., 268 *J. Biol. Chem.* 3538–3545 (1993). The trimeric s-bSR-I receptor contained all four extracellular domains of the intact receptor and exhibited the same broad binding specificity as the full length integral membrane form of the receptor.

CHO cells were grown in medium A, which consisted of Ham's F-12 medium (Gibco BRL, Gaithersburg, Md.) supplemented with 100 units/ml penicillin (Gibco BRL), 100 µg/ml streptomycin (Gibco BRL), and 2 mM glutamine (Gibco BRL) containing 5% (vol/vol) fetal calf serum (medium B). Transfected cells were grown in medium B containing 0.5 mg/ml G418. All mammalian cell incubations were performed in a humidified 5% $CO_2$/95% air incubator at 37° C.

[$^{35}$S]methionine-labeled conditioned medium was prepared from transfected CHO[s-bSRI]-A2 cells and untransfected CHO cells. The media were designated [$^{35}$S]s-bSR-I medium (containing s-bSR-I) and [$^{35}$S]control medium (containing no s-bSR-I) respectively. As described by D. Resnick et al., 268 J. Biol. Chem. 3538–3545 (1993), CHO[s-bSR-1]-A2 and untransfected CHO cells were plated at a density of 9×10$^5$ cells/100 mm dish in medium B. Cells were grown to 80% confluence (approximately 48 hours), washed, and metabolically labeled by addition of 4.5 ml of medium A prepared with methionine- and cysteine-free Ham's F-12 and supplemented with 0.2 mM L-cysteine, and 80 µCi/mi [$^{35}$S]methionine (Trans $^{35}$S-label with 70% methionine, purchased from ICN Biomedicals, Irvine, Calif.). After a 5 hour incubation at 37° C., supernatants were collected, and protease inhibitors and Buffer A+BSA (20 mM Tris base at pH 8.0/150 mM NaCl/1 mM $CaCl_2$; containing 2 mg/ml bovine serum albumin and 0.05% $NAN_3$) were added at final concentrations of 1 mM phenylmethylsulfonylfluoride (PMSF) (Sigma, St. Louis, Mo.), 1 µM leupeptin (Sigma), and 1 µM pepstatin (Sigma); 2:1 volume ratio of supernatant to buffer. The samples were then clarified by centrifugation (1000×g, 15 minutes, 4° C.) and stored in Falcon 2099 tubes that had been precoated with Buffer A+BSA.

c. Whole Cell Assay.

It was determined that a secreted form of the type I bovine MSRP (s-bSR-I) directly binds to the surface of a wide variety of whole Gram-positive bacteria.

Thirty minutes prior to binding assays, unlabeled L-methionine ((Sigma, St. Louis, Mo.) at 10 mM final concentration was added to suspensions of microorganisms grown as described above to minimize incorporation of free [$^{35}$S]methionine into microbial proteins during the assays. One ml assay mixtures containing 200 µl of bacterial suspension (approximately 2×10$^8$ bacteria), 50 µl of Buffer A (20 mM Tris base at pH 8.0/150 mM NaCl/1 mM $CaCl_2$), and 750 µl of either [$^{35}$S]s-bSR-I or [$^{35}$S]control medium were prepared in microcentrifuge tubes and incubated overnight on a rotator at 4° C. Maleylated bovine serum albumin (M-BSA) was coupled to CNBr-activated Sepharose™ (Pharmacia Fine Chemicals, Piscataway, N.J.) at approximately 3 mg M-BSA/mi hydrated resin. Suspensions of M-BSA-coupled Sepharose™ beads (M-BSA beads) (25 µl) were used in place of microorganism suspensions as positive controls.

After the overnight incubation, the bacteria or beads were pelleted by centrifugation in a microcentrifuge at 12,500×g for 5 minutes at 4° C. and washed twice with cold buffer A. In experiments examining the ability of LTA to inhibit the binding of the s-bSR-I to M-BSA beads, the beads were allowed to settle by gravity before each washing step, to prevent pelleting of LTA micelies. The washed pellets were then resuspended in SDS-PAGE sample buffer containing 2% β-mercaptoethanol, boiled for 5 minutes, and insoluble material was removed by centrifugation at 12,500×g for 2 minutes. The reduced samples were fractionated by electrophoresis through 10% polyacrylamide gels, as described by Resnick et al. (1993), and the labeled proteins were visualized by autoradiography with Kodak X-AR film. Prior to autoradiography, the gels were impregnated with either 0.125 M sodium salicylate (Sigma, St. Louis, Mo.) in 30% (v/v) methanol or autofluor (National Diagnostics, Mannville, N.J.).

When Streptococcus pyogenes strain T1/195/2 was incubated with [$^{35}$S]s-bSR-I medium and the results analyzed, the most prominent of the labeled proteins bound to the bacteria was approximately 78 kD, the mass of s-bSR-I (Resnick, et al., 1993). This protein was absent from S. pyogenes incubated with [$^{35}$S]control medium, and these binding data were similar to data for the binding of [$^{35}$S]s-bSR-I to Sepharose™ beads covalently derivatized with the MSRP ligand maleylated BSA (M-BSA beads. Therefore, one can conclude that the 78 kD binding protein was [$^{35}$S]s-bSR-I. Because the labeled MSRP in [$^{35}$S]s-bSR-I medium represented only a small fraction of the total labeled protein, yet it was a major component of the bound proteins, [$^{35}$S]s-bSR-I binding to S. pyogenes appears to have been specific. Binding was not dependent on bacterial protein synthesis or bacterial viability, because binding was neither decreased by preincubation of the organisms with either 50 µg/ml chloramphenicol or 0.05% (w/v) $NaN_3$ nor by killing the organisms by incubation at 60° C. for 10 minutes prior to the assay. In preliminary studies, the binding of a soluble form of the type II bovine MSRP, as well as soluble forms of human type I and II MSRP, to Gram-positive bacteria was also observed.

The polynucleotide ligand polyGuanosine (poly G, Sigma, St. Louis, Mo.) is an efficient competitive inhibitor of the binding of other polyanionic ligands to the cationic collagenous binding domain on the type I and type II MSRP. It was determined that the binding of S. pyogenes by s-bSR-I resembled the binding of other ligands to s-bSR-I. When poly G (400 µ/ml) was added to the assay mixture, analysis by SDS-PAGE showed that the binding of S. pyogenes to s-bSR-I resembled binding of other ligands in that poly G was an effective competitor. Thus, it appears that the binding of [$^{35}$S]s-bSR-I to S. pyogenes occurred via interactions of negatively charged components of the bacterial surface with the positively charged collagenous domain of the soluble receptor. This binding was not restricted to the T1/195/2 strain of S. pyogenes.

Table I illustrates the strains of Gram-positive bacteria that bound [$^{35}$S]secreted type I bovine MSRP. As in the T1/195/2 experiments described above, labeled bacterial components were incubated overnight at 4° C. in [$^{35}$S] methionine labeled media from transfected CHO cells expressing the truncated, soluble secreted soluble type I bovine macrophage scavenger receptor (s-bSR-I) or from untransfected controls, washed, dissolved by boiling in reducing sample buffer, and electrophoresed in a 10% polyacrylamide gel.

TABLE 1

Strains of Gram-Positive Bacteria That Bound [$^{35}$S] secreted Type I Bovine MSRP.

| Streptococcus pyogenes | Staphylococcus aureus |
|---|---|
| T1/195/2 | Reynolds |
| S43/192/4 | IL236 |
| J17E/165/3 | JL240 |
| T2/44/RB4/119 | Becker |
| T22/76/2 | JL252 |

TABLE 1-continued

Strains of Gram-Positive Bacteria
That Bound [$^{35}$S] secreted Type I
Bovine MSRP.

| | |
|---|---|
| T28/51/4-4 | |
| T28/150A/5 | *Streptococcus agalactiae* |
| | A909 |
| JRS75 | COH 31-15 |
| JRS4 | 110 |
| | 181 |
| 87-282 | |
| TX4 | |
| *Streptococcus mutans* ATCC 25175 | |
| *Enterococcus hirae* ATCC 9790 | |
| *Listeria monocytogenes* ATCC 43251 | |
| *Bacillus subtilis* ATCC 6633 | |

SDS-PAGE and the results illustrated in Table I showed that a total of eleven *S. pyogenes* strains, representing seven different M protein types bound [$^{35}$S]s-bSR-I. Thus, [$^{35}$S]s-bSR-I binding is a general characteristic of *S. pyogenes* that is not strain specific.

EXAMPLE 4

Determination that macrophages expressing MSRP bind microbes (cell binding assay).

The ability of poly G to inhibit *S. pyogenes* binding was used in experiments to examine the interaction of FITC-labeled pyogenes (strain T1/195/2) with a cultured murine macrophage-like cell line, P388D1, shown previously to express MSRP by J. Ashkenas et al., 34 *J. Lipid Res.* 983–1000 (1993).

P388D1 cells were maintained in dishes in Ham's F-12 with 10% fetal calf serum, 100 units/ml penicillin, and 100 µg/ml streptomycin. For experiments, approximately 12,500 cells were plated on 1 cm glass cover slips, in media lacking antibiotics. Cells were allowed to adhere for at least 24–36 hours, then washed in Ham's F-12 containing 10% fetal calf serum. *S. pyogenes*, either unlabeled or FITC-labeled, was added (final dilution of 1:250 from a stock solution of O.D.$_{600}$=1.0) in the presence or absence of varying concentrations of poly G. Mixtures were incubated for 30 minutes at 37° C. in 5% CO$_2$, then washed three times in PBS, and fixed with 100% cold methanol. Samples containing non-FITC labeled organisms were Gram-stained, then cover slips were mounted with Moviol and DAPCO. Slides were viewed in blinded fashion by two observers using fluorescence and phase contrast microscopy and a Nikon Microphot FXA epifluorescence microscope. The results (bacteria bound per 100 P388D1 cells) represent the means ± standard deviations determined from three experiments in which at least 100 P388D1 cells were counted for each condition.

After the 30-minute incubation at 37° C., binding of 72±8 bacteria/100 P388D1 cells was observed. When poly G at concentrations of 2, 20, or 200 µg/ml was included in the incubation medium, the number of cell associated bacteria/100 P388D1 cells was reduced to 43±4, 28±9, and 22±5, respectively. Similar results were obtained when binding of unlabeled bacteria was assessed by Gram staining. These results indicate that association of *S. pyogenes* with intact cultured murine macrophages is mediated in part by their full length, cell surface MSRP.

EXAMPLE 5

Method for determining that s-bSR-I binds to *S. pyogenes* strains lacking M protein or hyaluronic acid capsules.

Using mutant strains of *S. pyogenes*, it was determined that the binding of MSRP to *S. pyogenes* was independent of the hyaluronic acid capsule and the M protein, two well characterized virulence determinants.

As described in Example 3, bound macrophage scavenger receptor from strains of *S. pyogenes* was incubated overnight at 4° C. in [$^{35}$S]methionine labeled media from transfected CHO cells expressing the truncated, soluble secreted type I bovine macrophage scavenger receptor (s-bSR-I), washed, dissolved by boiling in reducing sample buffer, electrophoresed in a 10% polyacrylamide gel, and visualized by autoradiography. *S. pyogenes* M-protein positive (T28/150A/5) and negative (T28/51/4-4) strains and *S. pyogenes* hyaluronic acid and capsule positive (wild type 87–282) and negative (TX-4) strains were used. Autoradiography showed that the type 28 *S. pyogenes* strain and its spontaneous M protein-negative mutant bound s-bSR-I equivalently. Similar results were obtained from the assays using the type 6 M protein-negative transposon mutant of *S. pyogenes* and its wild type parent strain (Table I, strains JRS75 and JRS4). Thus, the M protein is not necessary for binding. The data also show that the wild type *S. pyogenes* strain 87–282 and its acapsular, hyaluronic acid-negative, transposon mutant, TX4, bound [35S]s-bSR-I equally well. In addition, at least five of the *S. pyogenes* strains shown in Table I that bound [35S]s-bSR-I lack hyaluronic acid capsules. Furthermore, growth of *S. pyogenes* organisms to stationary phase both reduced capsule production and increased MSRP binding. Therefore, it is unlikely that the hyaluronic acid capsule played a significant role in binding to s-bSR-I.

Isogenic capsule-minus transposon mutants of *S. agalactiae* and *S. aureus* also bound [$^{35}$S]s-bSR-I equivalently or better than the parent strains, again indicating that the capsule plays little, if any, role in [$^{35}$S]s-bSR-I binding. In preliminary experiments, it was also observed that purified native and deacylated LTA from *S. agalactiae* and *S. aureus* respectively (obtained from Steve Mattingly, University of Texas, San Antonio Tex., and Jean Lee, Harvard University, Boston, Mass., respectively) inhibited binding of [$^{35}$S]s-bSR-I to poly-G beads in a dose dependent fashion. In contrast to the results with all other Gram-positive organisms examined, only minimal binding was observed to two encapsulated and one rough strain of *S. pneumoniae*, organisms with atypical LTAs.

EXAMPLE 6

Method for demonstrating that lipoteichoic acid (LTA) is a ligand for s-bSR-I.

The results in the previous experiments show that some other surface component must mediate binding of [$^{35}$S]s-bSR-I to *S. pyogenes*. Another major surface component of *S. pyogenes* is the polyanionic polymer lipoteichoic acid, described by I. Ofek et al., 141 *J. Exp. Med.* 990–1003 (1975), and by Kessler et al., 150 *J. Exp. Med.* 1498–1509 (1979). A direct, genetics based test of the role of LTA in binding was not possible because no naturally occurring or genetically engineered strains of *S. pyogenes* lacking LTA are available. However, because binding of [$^{35}$S]s-bSR-I to *S. pyogenes* apparently occurs via interaction with the receptor's cationic collagenous ligand binding domain, it was possible to examine the potential role of LTA in mediating binding. This was done by determining that LTA functions as a competitive inhibitor of [$^{35}$S]s-bSR-I binding to other ligands, e.g., M-BSA beads.

Purified LTA from *S. pyogenes*, isolated as described by W. A. Simpson et al., 255 *J. Biol. Chem.* 6092–6097 (1980), was provided by James Dale and Harry Courtney (University of Tennessee, Memphis, Tenn.). Purified LTA was suspended in LTA buffer (0.25% deoxycholate, 0.2 M NaCl, 1 mM EDTA, 0.02% $NAN_3$, 10 mM Tris HCl, pH 8.0) prior to use.

FIG. 1 shows the results of an experiment in which increasing amounts of *S. pyogenes* LTA were added to mixtures of [$^{35}$S]methionine labeled medium from transfected CHO cells expressing the secreted receptor ([$^{35}$S]s-bSR-I medium) and M-BSA beads. The total assay volume was 0.25 ml instead of 1.0 ml, as described in the whole cell assay (Example 3), and each assay contained 50 μl of lipoteichoic acid (LTA) buffer with the indicated amounts of LTA and 10 μl of M-BSA beads. As described in Example 3, after an overnight incubation at 4° C., the adherent proteins were eluted from the beads by boiling in reducing sample buffer, bound [$^{35}$S]s-bSR-I was resolved by 10% polyacrylamide gel electrophoresis, and the relative amounts of bound [$^{35}$S]s-bSR-I were determined using a Molecular Dynamics Phosphorimager. All values shown were corrected for "nonspecific" background binding by subtracting the value determined in the presence of 400 μg/ml poly G. The amounts of MSRP binding shown in FIG. 1 were measured with a Molecular Dynamics Phosphorimager.

*S. pyogenes* LTA was an effective inhibitor of binding ($IC_{50}$=approximately 4 μg/ml). LTA also inhibited binding of [$^{35}$S]s-bSR-I to poly G beads, with a similar $IC_{50}$. Thus, LTA is a binding determinant on *S. pyogenes*. These data indicate that it is the major binding determinant.

LTA or analogous molecules are ubiquitous surface component of Gram-positive bacteria, as reviewed by W. Fischer, 29 *Adv. Microb. Physiol.* 233–302 (1988), and A. J. Wicken and K. W. Knox, 187 *Science* 1161–1176 (1975). The finding that LTA mediates binding of MSRP to *S. pyogenes* indicated that many, if not all, Gram-positive bacteria bind to MSRP. *Enterococcus hirae* 9790 and *Streptococcus agalactiae* were incubated overnight at 4° C. in [$^{35}$S]methionine labeled medium from transfected CHO cells expressing the truncated, soluble secreted type I macrophage scavenger receptor (s-bSR-I), with or without 400 μg/ml poly G, washed, dissolved by boiling in reducing sample buffer, electrophoresed in a 10% polyacrylamide gel, and visualized by autoradiography. [$^{35}$S]s-bSR-I bound to *Enterococcus hirae* and *S. agalactiae*, as well as to *S. pyogenes*. Poly G competed with the binding of receptor to the bacteria. In binding studies using a wide variety of Gram-positive bacteria, it was observed that all species and strains of bacteria tested bound [$^{35}$S]s-bSR-I (Table I). Binding was competitive with poly G although the extent of competition varied slightly between organisms. In addition to the species described above, [$^{35}$S]s-bSR-I bound to *Streptococcus mutans, Staphylococcus aureus, Listeria monocytogenes,* and *Bacillus subtilis*.

Modifications and variations of the method to treat Gram-positive septicemia will be obvious to those skilled in the art from the foregoing detailed description. Such modifications and variations are intended to come within the scope of the appended claims.

---

We claim:

1. A method for treating a patient having Gram positive bacterial septicemia comprising administering to the patient an effective amount of a macrophage scavenger receptor protein (MSRP) in a pharmaceutically acceptable carrier to inhibit activation of complement, cytokine release or nitric oxide production induced by lipoteichoic acid released by the Gram positive bacteria.

2. The method of claim 1 wherein the MSRP is a soluble macrophage scavenger receptor protein or a portion thereof binding to lipoteichoic acid.

3. The method of claim 2 wherein the portion is the collagen binding region.

4. The method of claim 1 wherein the macrophage scavenger receptor protein or a portion thereof is immobilized in an extracorporeal reactor and the patient is treated by passing blood through the reactor.

5. A pharmaceutical composition for inhibiting activation of complement, cytokine release or nitric oxide production induced by lipoteichoic acid released by Gram positive bacteria comprising a compound wherein the compound is MSRP or a portion thereof binding to lipoteichoic acid in a pharmaceutically acceptable carrier.

6. The composition of claim 5 wherein said portion of the macrophage scavenger receptor protein is the collagen binding region.

7. The composition of claim 5, wherein the compound is immobilized to an extracorporeal reactor.

8. The composition of claim 7, wherein the compound is immobilized to a substrate selected from the group consisting of chromatographic resins, assay wells, and test tubes.

* * * * *

UNITED STATES PATENT AND TRADEMARK OFFICE
CERTIFICATE OF CORRECTION

PATENT NO. : 5,624,904
DATED : April 29, 1997
INVENTOR(S) : Keith Joiner, Monty Kreiger It is certified that error appears in the above-identified patent and that said Letters Patent is hereby corrected as shown below:

Column 1, line 8, insert the following:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Thirteenth Day of April, 1999

Attest:

Q. TODD DICKINSON

*Attesting Officer*     *Acting Commissioner of Patents and Trademarks*